United States Patent [19]

Wang et al.

[11] Patent Number: 5,427,935
[45] Date of Patent: Jun. 27, 1995

[54] HYBRID MEMBRANE BEAD AND PROCESS FOR ENCAPSULATING MATERIALS IN SEMI-PERMEABLE HYBRID MEMBRANES

[75] Inventors: Henry Y. Wang, Ann Arbor, Mich.; Somesh C. Nigam, Bedminster, N.J.

[73] Assignee: The Regents of the University of Michigan, Ann Arbor, Mich.

[21] Appl. No.: 84,749

[22] Filed: Jun. 29, 1993

Related U.S. Application Data

[63] Continuation of Ser. No. 671,163, Mar. 14, 1991, abandoned, which is a continuation of Ser. No. 237,789, Aug. 29, 1988, abandoned, which is a continuation-in-part of Ser. No. 77,230, Jul. 24, 1987, abandoned.

[51] Int. Cl.$^6$ ............... A61K 9/16; B01J 13/20; B01J 13/22; C12N 11/04
[52] U.S. Cl. ............... 435/178; 264/4.1; 264/4.3; 264/4.32; 264/4.33; 424/418; 424/455; 424/463; 424/491; 424/493; 435/182; 435/240.22
[58] Field of Search ............... 264/4.1, 4.3, 4.32, 264/4.33, 4.7; 424/418, 455, 463, 491, 493; 435/175, 177, 178

[56] References Cited

U.S. PATENT DOCUMENTS

| | | | |
|---|---|---|---|
| 3,522,346 | 7/1970 | Chang | 424/491 |
| 3,549,555 | 12/1970 | Hiestand et al. | 264/4.3 X |
| 3,725,113 | 4/1973 | Chang | 192/52 |
| 3,730,841 | 5/1973 | Salvatore et al. | 435/182 |
| 3,860,490 | 1/1975 | Guttag | 435/182 |
| 3,954,678 | 5/1976 | Marquisee | 252/62.53 X |
| 3,972,776 | 8/1976 | Vieth et al. | 435/177 |
| 4,001,480 | 1/1977 | Shank | 428/411.1 |
| 4,076,774 | 2/1978 | Short | 264/4 |
| 4,148,689 | 4/1979 | Hino et al. | 435/182 |
| 4,251,387 | 2/1981 | Lim et al. | 264/4.3 |
| 4,255,411 | 3/1981 | Lim et al. | 424/1.1 |
| 4,257,884 | 3/1981 | Lim | 435/182 X |
| 4,322,311 | 3/1982 | Lim et al. | 264/4.7 |
| 4,324,683 | 4/1982 | Lim et al. | 264/4.3 |
| 4,334,027 | 6/1982 | Klein et al. | 435/178 |
| 4,352,883 | 10/1988 | Lim | 435/178 |
| 4,386,895 | 6/1983 | Sodickson | 264/4 |
| 4,389,330 | 6/1983 | Tice et al. | 427/213.36 |
| 4,389,419 | 6/1983 | Lim et al. | 264/4.1 X |
| 4,391,909 | 7/1983 | Lim | 435/178 |
| 4,407,957 | 10/1983 | Lim | 435/178 |
| 4,409,331 | 10/1983 | Lim | 435/178 |
| 4,495,288 | 2/1985 | Jarvis, Jr. et al. | 435/241 |
| 4,615,883 | 10/1986 | Nelson et al. | 424/84 |
| 4,639,423 | 1/1987 | Kahlert et al. | 435/287 |
| 4,647,536 | 3/1987 | Mosbach et al. | 435/177 |
| 4,744,933 | 5/1988 | Rha et al. | 264/4.3 |
| 4,749,620 | 5/1988 | Rha et al. | 428/402.2 |

FOREIGN PATENT DOCUMENTS

| | | | |
|---|---|---|---|
| 0152898 | 8/1985 | European Pat. Off. | 428/321.5 |
| 3432923A1 | 3/1986 | Germany . | |
| 0078634 | 5/1985 | Japan | 424/493 |
| 1163023 | 9/1969 | United Kingdom | 264/4.1 |
| 2122490 | 1/1984 | United Kingdom | 424/493 |

OTHER PUBLICATIONS

Nilsson, K. et al., "Entrapment of Animal Cells for Production of Monoclonal Antibodies and Other Biomolecules", *Nature*, vol. 302, Apr. 14, 1983, pp. 629–630.

Lim et al:, "Microencapsulation of Living Cells and Tissue", *J. Pharm. Sci.*, vol. 70, No. 4, Apr., 1981, pp. 351–354.

(List continued on next page.)

*Primary Examiner*—Richard D. Lovering
*Attorney, Agent, or Firm*—Harness, Dickey & Pierce

[57] ABSTRACT

Material such as biological material is encapsulated within a semi-permeable hybrid membrane bead by suspending the material in a medium which comprises an effective amount of a gelling inducer; forming said suspension into a droplet of a size sufficient to envelop said material, suspending a second material in a gelling solution comprising an effective amount of a gel forming polymer which gels upon contact with said gelling inducer forming a discrete bead by contacting the outer surface portion of the droplet with a gelling solution, and allowing the gelling solution to thicken sufficiently for the second material to become entrapped therein.

37 Claims, No Drawings

OTHER PUBLICATIONS

Howell, S. L., et al., "Possible Use of Agarose Gels as Encapsulating Media for Transplantation of Islets of Langerhans", *Proc. Physiol. Soc.*, Nov., 1981, pp. 20P–21P.

Gharapetian, H., et al., "Encapsulation of Viable Cells within Polyacrylate Membranes", *Biotech. Bioeng.*, vol. 28, Oct., 1986, pp. 1595–1600.

Chang, T. M. S., "Biodegradable Semipermeable Microcapsules Containing Enzymes, Hormones and other Biologicals", *J. Bioeng.*, vol. 1, 1976, pp. 24–32.

Posillico, E. G., "Microencapsulation Technology for Large-Scale Antibody Production", *Biotech.*, vol. 4, Feb., 1986, pp. 114–117.

Klausner, A., "Monoclonal Makers Upping Production, Vying for New Contracts", *Biotech.*, Nov., 1983, pp. 736–640.

Chemical Abstracts, vol. 79, No. 25, Dec. 24, 1973 (Columbus, Ohio) p. 218, Abstract 145072r, & JP, A 7316183 (Snow Brand Milk Products Co., Ltd.) May 19 1973.

Biotechnology and Bioengineering, vol. 27, No. 2, Feb 1985, ± John Willey & Sons, Inc. (New York) Goosen M. F. A. et al.: "Optimization of microencapsulatio parameters: semipermeable microcapsules as a bio-artificial pancreas", pp. 146–150, pp. 146–147, Material and methods. Microencapsulatio of living cells; p. 147 Dependence of microcapsule morphology on sodiun alginate viscosity and purity.

Spiekermann, K. D., et al., "Animal Cells Encapsulate Within Ca-Alginate Hollow-Spheres", *Proc. 4th Eurc Conf. Biotech.*, vol. 3, Oct. 1, 1987, pp. 590–593.

HYBRID MEMBRANE BEAD AND PROCESS FOR ENCAPSULATING MATERIALS IN SEMI-PERMEABLE HYBRID MEMBRANES

This invention was made with Government support under Grant No. CBT-8416543 awarded by the National Science Foundation. The Government has certain rights in the invention.

This is a continuation of U.S. patent application Ser. No. 07/671,163, filed Mar. 14, 1991, now abandoned, entitled "Hybrid Membrane Bead and Process for Encapsulating materials in Semi-permeable Hybrid Membranes" by Henry Y. Wang and Somesh C. Nigam; which is a continuation of Ser. No. 07/237,789, filed Aug. 29, 1988, entitled "Hybrid Membrane Bead and Process for Encapsulating materials in Semi-permeable Hybrid Membranes," Henry Y. Wang and Somesh C. Nigam (now abandoned); which is a continuation-in-part of Ser. No. 07/077,230, filed Jul. 24, 1987, entitled "Encapsulation of Biological Materials in Semi-permeable Membranes," by Somesh C. Nigam and Henry Y. Wang (now abandoned).

BACKGROUND OF THE INVENTION

The present invention relates to encapsulated products. More particularly, the present invention relates to a hybrid membrane bead and process for the encapsulation of bioactive materials in semi-permeable hybrid membrane beads of gel forming polymers.

Encapsulation processes are finding increasing use in a variety of areas of biotechnology. Such processes are used to encapsulate various materials such as enzymes, hormones, drugs, adsorbents and cells which can then be used in bioreactors, artificial organs, bioseparation systems, controlled drug-release systems, and so forth. Prior art processes often require harsh conditions such as the use of non-aqueous solvents, extremes of pH, or high temperature. Such techniques are inherently unsuitable for encapsulating delicate biological materials such as live cells and labile proteins.

Ideally, encapsulation techniques for biological materials should use mild conditions and a membrane material which is inert and non-toxic to the material being encapsulated. The encapsulation technique should also provide a semi-permeable membrane and allow for adjustment of membrane thickness and membrane pore size. Preferably, the charge on the membrane should be adjustable to suit different applications. The membrane should also be strong enough to withstand liquid-shear or the friction effects arising out of agitation.

A well known membrane encapsulation method is the poly (L-lysine) —alginate membrane method which involves formation of a polyelectrolyte membrane complex. In this method the mixture of bioactive material and sodium alginate is extruded through a droplet forming device into a buffer containing calcium chloride. The $Ca^{+2}$ cations cross-link the alginate matrix almost instantaneously to form gel beads. The beads are then treated with poly-1-lysine to displace the calcium ions in the outer layer to form a polyelectrolyte-complex membrane. Calcium alginate gel in the interior of the bead is then liquefied using a calcium chelating agent.

However the poly (L-lysine) alginate method of membrane encapsulation involves a large number of processing steps and results in a membrane which is charged due to its polyelectrolyte nature. Also, the membrane formed has relatively poor mechanical strength and poor chemical stability in the presence of electrolytes such as heparin, polysulfonic acid and polyphosphoric acids which interact more strongly with alginate or poly (L-lysine). Furthermore, liquefied alginate remaining within the membrane bead may pose certain problems. For example, alginate can interfere with the functioning of biomaterial by complexing with multivalent ions or other charged macromolecules. Alginate can also adsorb on positively charged surfaces and cause fouling. In addition, this and other methods of encapsulation are capable of immobilizing only one population of biological material evenly distributed through the gel matrix or bead.

Thus, there remains a need for an improved process for encapsulation of bioactive materials and it is an object of the present invention to provide such an improved process. It is another object of the invention to provide a membrane bead and process of encapsulation which can immobilize more than one biological population and/or populations at different concentrations or with different distributions within the membrane bead. Further understanding of this invention will be had from the following description and claim. All parts and percentages herein are by weight unless otherwise indicated.

SUMMARY OF THE INVENTION

In accordance with the present invention, the desired materials are encapsulated within a semi-permeable membrane by a process comprising the steps of:

suspending a first material to be encapsulated in a medium which is compatible with the material and which comprises a small, effective and diffusible gelling inducer such as $Ca^{+2}$, $K^+$, polyphosphate, etc.;

forming said suspension into a droplet of a size sufficient to envelop said material, said droplet having an outer surface layer;

suspending a second material to be encapsulated in a gelling solution which is compatible with the material, said gelling solution comprising an effective amount of a gel forming polymer which gels on contact with said gelling inducer; and forming a discrete membrane bead by contacting said outer surface layer with said gelling solution for a time sufficient for said gelling solution to gel to a desired thickness, said thickness of said gel being sufficient to entrap said second material therein.

Thus, a hybrid multicompartment membrane bead or capsule is formed—one compartment being the "hollow" interior compartment of the bead and the other being the thickened gel membrane matrix. The hollow interior compartment may or may not contain a mechanical support.

Optionally, the outer surface layer of the membrane bead can be coated with a second polymer to form a composite membrane. Alternatively, the gelling solution comprises an effective amount of a second gel forming polymer in addition to the first gel forming polymer. The membrane beads formed after the gelation of the first polymer can be removed from the polymer solution. The physico-chemical conditions can be altered to induce the gelling of the second polymer entrapped within the membrane compartment of the membrane bead.

DETAILED DESCRIPTION OF THE INVENTION

In accordance with the present invention, a gel forming polymer system is used to form a semi-permeable hybrid membrane bead encapsulating various materials. It will be appreciated that the process of this invention is particularly well suited for use in encapsulating biological materials. Thus, the description of the preferred embodiments of this invention is in the context of encapsulating biological materials. However, the process of this invention can also be used to encapsulate other materials such as magnetites or other inorganic matter and such other uses are contemplated to be within the broad scope of this invention.

The biological materials to be encapsulated can be tissue, organelle, plant or animal cells, delta cells, whole islet of Langerhans, hepatocytes, bacteria, algae, fungi, viruses, proteins, pharmaceutical compounds and so forth. The material must be of a size small enough to be suitable for encapsulation by the droplet method of this invention but can vary widely in diameter from less than a micron to several millimeters. The present process allows viable cells to be encapsulated in a semi-permeable membrane allowing cells access to nutrients and other substances necessary for viability but protecting cells from substances having a molecular weight above a selected size such as antibodies, toxins and bacteria. Thus the biological material can be maintained in a viable state for an extended period of time.

The first biological material to be encapsulated is initially suspended in an aqueous medium which is physiologically compatible with the material. The medium should comprise required nutrients, be without toxic substances and have a suitable pH as, for example, a typical buffered solution. The medium also comprises an effective amount of a gelling inducer. The gelling inducer is of a type and in an amount effective to diffuse outwardly and cause the gel forming polymer to gel when coming into contact therewith as described in more detail hereinafter. Optionally, the aqueous medium also comprises a viscosity enhancer such as dextran, hyaluronic acid, polyethylene glycol, starch and the like.

Optionally, the aqueous medium may also contain mechanical support particles. The purpose of the mechanical support is to anchor the material being encapsulated or to enhance the mechanical strength of the membrane bead. The mechanical support particles can be porous or non-porous. Suitable mechanical supports include Celite, porous glass, polymeric or metallic sponges, and the like.

The suspension of the first material being encapsulated is then formed into droplets of a size sufficient to envelop the material by, for example, dropping the suspension through a fine nozzle, capillary tube or hypodermic needle. This method is amenable for delicate biological materials. Alternatively, the material being encapsulated can be pelletized using a punch-press type apparatus or using a pellet mill for large scale applications. As yet another alternative, the material being encapsulated can be extruded in the form of fibers or other shapes.

The second material to be encapsulated is suspended in a solution compatible with the material and containing an effective amount of a gel forming polymer which gels upon contact with the gel inducer. The solution containing the second material is then contacted with the droplet or pellet containing the first material and gel inducer. The outer surface layer of the droplet or pellet containing the first material is almost instantly provided with a gelled semi-permeable membrane upon contact of the outer surface layer with the solution of second material containing gel forming polymer. The gelled membrane containing the second material is then allowed to thicken to a desired thickness sufficient to entrap the desired amount of second material in the hybrid membrane bead.

The gel forming polymer can be any non-toxic water soluble gel forming polymer which forms a gel upon contact with a gelling inducer and is compatible with the second material to be encapsulated. Optionally, the gel forming polymer is an ionotropic gel forming polymer such as a water soluble polysaccharide. Suitable polysaccharides include those typically extracted from vegetable matter and include sodium alginate, guar gum, gum arabic, carrageehan, pectin, tragacanth gum, xanthan gum, and deacylated chitin (chitosan). Upon contact with gel inducers the polysaccharide molecules form a water-insoluble shape-retaining gel membrane bead.

It is an advantage of this invention that the gel forming polymer comes in contact only with the outer surface portion of the droplet before gelling. There is thus little, if any, effect of the polymers on the first material being encapsulated which stays in its original environment in the suspension.

If the type of membrane formed using the initial gelation is adequate for the particular bioprocessing application desired, the membrane beads can be recovered from the gelling solution and equilibriated with the desired media. However, the mechanical and chemical properties of the bead membrane can be further altered to suit different bioprocessing and biomedical applications.

In order to alter the membrane a second gel forming polymer can be used to impart altered properties to the membrane such as mechanical strength, chemical stability, pore size and/or surface charge. The second polymer can be another polyelectrolyte having opposite charge to that of the first polymer. In this case the second polymer can be coated on the outer surface of the membrane bead to complex with the initial gel membrane. The resulting polyelectrolyte complex imparts greater chemical stability to the membrane bead. For example, sodium alginate membrane beads can be coated with polycations such as poly (L-lysine), polyethylene-imine, chitosan or acrylate/methacrylate copolymers (Eudragit RL 100 from Rohm GmbH, Darmstadt, FRG) to form beads having composite membranes. It is possible to obtain membrane beads with desired charge characteristics on either side of the membrane.

Alternatively, the gel forming solution comprises a solubilized second gel forming polymer in addition to the first polymer. The gelling of the first gel forming polymer to form the initial membrane can be used to entrap the second gel forming polymer in the membrane.

Due to high viscosity some polymer solution may adhere to the exterior of the membrane bead surface when it is removed from the gelling solution. The membrane beads can be placed in an oil medium or in a buffer solution containing gelling inducer for the first and/or second polymer. Both of these approaches curtail any loss of the thin liquid polymer solution film covering the membrane bead. It will be apparent to those skilled in the art that the physico-chemical conditions of the membrane bead can be altered in various ways to induce gelling of the second polymer.

Optionally, the second gel forming polymer can be a thermal gel forming polymer. Thermal gel forming polymers undergo gelation when their temperature is lowered below their gelation temperatures and generally have chemical and mechanical properties which are superior to ionotropic gels. Though widely used in gel entrapment, currently no method exists for membrane encapsulation using thermal gels. A wide variety of thermal gel forming polymers can be used in the present invention, including, for example, agarose and kappa-carrageenan.

If desired, the first polymer component of the composite membrane can be removed by means well known in the art. For example, if the first polymer is an ionotropic gel forming polymer, its dissolution can be achieved by contacting the membrane bead with a chelating agent after the gelling of the second polymer is complete.

It will be appreciated that the present process is versatile and subject to substantial variation. The membrane can be formed using a wide variety of available gel forming polymers. Membranes of different characteristics can be obtained by manipulating the type and the concentration of the polymers. Aqueous thermal gels such as agarose, k-carrageenan, or gelatin may be employed to encapsulate delicate materials such as live cells and labile proteins. If the materials being encapsulated are relatively stable in the presence of organic solvents, reactive cross-linking agents and extremes of pH for short durations of time, the list of polymers useful herein can be further expanded to include precipitation gels (eg. cellulose acetate), polycondensation gels (eg. epoxy and polyurethanes) and copolymerized gels (eg. polyacrylamides). The hybrid membrane beads formed using these polymers can be used to encapsulate adsorbents, drugs and stable enzymes in membranes of greater structural rigidity and chemical inertness.

It should also be appreciated that, although the materials encapsulated in the hybrid membrane bead are discussed as a first and second material, the materials inmobilized in the gel membrane and in the interior of the membrane bead may be the same material. In this way, two discrete populations of the material can be immobilized within the membrane bead at different concentrations or densities. It should also be noted that a membrane capsule in which materials are encapsulated only in the interior using a thin semi-permeable membrane, represents just one special case of the hybrid membrane bead described in this invention.

The utility of the hybrid membrane bead of the present invention is virtually unlimited. For example, the membrane bead can be used to immobilize different difficult to grow animal cell lines which require feeder cells to provide nutrients for growth. The cells can be grown in the hollow matrix of the bead while the feeder cells are immobilized and grown in the gel matrix/membrane. As another example, a small amount of magnetite can be immobilized inside the gel membrane so the membrane bead with other materials encapsulated in its interior can be retrieved by magnetizing the bead under the influence of a magnet.

The membrane bead of the invention can, for example, also be used in anaerobic biological waste treatment. An oxygen sensitive enriched methanotropic cell population can be immobilized in the interior of the membrane bead while the acetogenic cell population is immobilized in the gel membrane. The waste substrates converted into volatile fatty acids and acidic products will diffuse into the inner compartment and be converted to methane gas by the methanotrops. The methanotrops will be protected from free oxygen in the waste stream by the acetogens.

As yet a further example, an NADH-dependent enzyme can be entrapped within the interior of the membrane bead, while another NADH-generating enzyme is immobilized in the gel membrane. Thus a coupled membrane bead where NADH can be consumed and generated simultaneously within the same membrane bead.

EXAMPLE 1

This example illustrates formation of calcium alginate membrane beads containing material to be encapsulated. A solution containing 0.8% sodium alginate (Sigma A 7128, type IV) is prepared and kept stirred using a magnetic stirrer at room temperature. An aqueous suspension containing the material to be encapsulated is prepared in 0.1M HEPES buffer (pH 7) with 0.1M $CaCl_2$ and 20% dextran (Sigma D 4133). The suspension is dropped through a hypodermic needle to form droplets which fall into rapidly stirred alginate solution. A capsular membrane forms almost instantaneously around the suspension drop due to the cross-linking of the interfacial alginate molecules by $Ca^{+2}$ cations. Prior to the removal of the membrane beads the polymer solution is diluted five-fold by adding required amount of 0.1M HEPES buffer (pH 7). This step dilutes the alginate solution outside the membrane beads and reduces the possibility of membrane beads joining each other when they are in close contact, due to the gelation of the alginate solution on their exterior surface. Capsules are removed from the solution and excess solution is drained using an appropriate size mesh. The membrane beads are transferred to 0.1M HEPES buffer (pH 7) containing 0.1M $CaCl_2$ and incubated for one minute to stabilize the exterior surface. Finally membrane beads are equilibriated with the desired media.

EXAMPLE 2

This example illustrates formation of agarose membrane beads containing the desired material. A solution containing 0.5% agarose (Sigma A 4018, type VII) and 0.25% sodium alginate (Sigma A 7128, type IV) is prepared and kept warm and stirred using a magnetic stirrer at 40° C. An aqueous buffered suspension containing the biological material is prepared with 0.1M $CaCl_2$. The viscosity of this suspension is increased by adding 20% dextran (Sigma D 4100). The suspension is dropped through a hypodermic needle to form droplets which fall into the alginate/agarose solution. A capsular membrane fores almost instantaneously around the suspension drop due to the cross-linking of the interfacial alginate molecules by $Ca^{+2}$ cations. The formed membrane beads are separated and shaken vigorously in oil medium at 95° C. whereupon agarose in and around the membrane surrounding the drop solidifies and the interfacial tension at the gel-oil interface gives rise to a smooth and uniform exterior surface. The membrane beads are then equilibrated in a buffer containing 0.05M EDTA, which is $Ca^{+2}$ chelating agent, which liquifies and removes Ca-alginate component of the gel membrane. Finally membrane beads are washed and placed in the desired media.

The membrane beads thus formed were found to be reasonably strong due to the presence of agarose in the membrane matrix. The membrane beads were also found to be stable in solutions containing high concentrations of NaCl, EDTA, Phosphate etc.

EXAMPLE 3

This example illustrates the formation of chitosan membrane beads containing the desired material. 0.5% chitosan (Sigma C 3646) is dissolved in water containing 0.5% (v/v) acetic acid. Material to be encapsulated is mixed with 1.5% sodium-tri-poly-phosphate solution (pH 5.5) containing 40% dextran (Sigma D 4133). This suspension is extruded through a hypodermic needle connected to an air-jet for generating small droplets (0.5–1.0 mm diameter) of the viscous suspension. Droplets instantly form a chitosan polyphosphate membrane enclosing the droplet. Capsules are removed from the solution and further treated in 1.5% sodium-tri-polyphosphate solution (pH 8.5) for a half hour. Finally the membrane beads are equilibrated in the desired buffer.

EXAMPLE 4

This example illustrates encapsulation of mammallian cells in alginate/poly-(L-lysine) membrane beads. KB cells are suspended in a solution consisting of 10% dextran, 1.3% $CaCl_2$ buffered with 13 mM HEPES (pH 7) at a concentration of $10^5$ cells/ml. The solution is extruded through an atomizer into rapidly stirred 0.25% sodium alginate solution (KELCO, LV) in isotonic NaCl solution. The membrane beads containing KB cells thus formed are removed after diluting the solution five fold using isotonic NaCl solution. The membrane beads are subsequently exposed to a 0.05% poly (L-lysine) solution for 5 minutes to strengthen the membrane beads. Finally membrane beads are removed and washed with isotonic solution to remove extra poly (L-lysine) before equilibriating with the desired media. Cells encapsulated using this method remain viable and show normal growth.

EXAMPLE 5

This example illustrates the formation of a gelatin/alginate hybrid membrane bead suitable for the encapsulation and growth of anchorage dependent mammallian cells inside the capsules. The presence of gelatin in the thickened gel membrane allows favorable conditions for the attachment and proliferation of mammallian cells. A solution containing 0.5% (w/v) gelatin (Sigma G 2500 Type A) and 0.5% sodium alginate (Sigma A 7128, type IV) is prepared by using a 25 mM HEPES buffer (pH 7). An aqueous suspension containing the material to be encapsulated is prepared in 25 mM HEPES buffer (pH 7) with 3% (w/v) calcium chloride and 20% dextran (Sigma D 4133). The suspension is dropped into a well stirred gel at in/alginate mixture solution. A capsule membrane forms instantaneously around the droplet due to the cross-linking of calcium alginate gel. The capsule membrane is allowed to thicken for 5 minutes. Gelatin molecules are entrapped in the thickened capsule membrane matrix. Membrane beads thus formed are transferred to 25 mM HEPES buffer (pH 7) containing 0.5% $CaCl_2$ and incubated for 1 hour to stabilize the gel membrane of the hybrid membrane bead. Finally membrane beads are removed and equilibriated with the desired media.

EXAMPLE 6

This example illustrates the formation of magnetically susceptible hybrid alginate/magnetite membrane beads. In the first step of the process dried barium alginate/magnetite powder is prepared. In the second step alginate/magnetite powder is entrapped in the thickened wall of hybrid alginate membrane beads.

Magnetite suspension is prepared by mixing 12.8 g of $FeCl_2.4H_2O$ in 1600 ml distilled water. The black magnetite precipitate was washed with distilled water twice and the volume of the suspension was adjusted to form an 8% magnetite suspension. Alginate/magnetite solution was prepared by mixing 8% magnetite suspension with an equal volume of 2% sodium alginate solution. The mixture was passed through a hypodermic needle (18 G) dropping into 0.2 M $BaCl_2$ solution to form the gel beads. The gel beads were stabilized by treating with glutaraldehyde in the presence of polyethyleneimine to avoid dissolution. In brief the beads were suspended in 0.5% (w/v) polyethyleneimine-HCl in 50 mM $CaCl_2$ (pH 7) for 24 hours at room temperature with stirring. The gel beads were washed briefly with $H_2O$ and subsequently incubated in 1% (v/v) glutaraldehyde, 10 mM sodium phosphate (pH 7) at room temperature for 1 minute with stirring. The preparation was washed in $H_2O$ and air-dried at room temperature. Dried alginate/magnetite powder with particle diameters between 0.01 mm and 0.1 mm were obtained by crushing the dried preparation.

Dried alginate/magnetite powder was mixed with 1% sodium alginate (Sigma A 7128, type IV) to give a final concentration of 5% (w/v). An aqueous suspension containing the material to be encapsulated is prepared in 25 mM HEPES buffer (pH 7) with 3% (w/v) calcium chloride and 20% dextran (Sigma D 4133). The suspension is dropped into a well stirred alginate solution containing suspended particles of alginate/magnetite powder. A capsule membrane forms instantaneously around the droplet due to the cross-linking of calcium alginate gel. The capsule membrane is allowed to thicken for 5 minutes. Alginate/magnetite particles are entrapped in the thickened capsule membrane matrix. Magnetically susceptible hybrid membrane beads thus formed are transferred to 25 mM HEPES buffer (pH 7) containing 0.5% $CaCl_2$ and incubated for one hour to stabilize the gel membrane of the hybrid membrane bead. Finally membrane beads are removed and equilibrated with the desired media.

EXAMPLE 7

This example illustrates the format ion of calcium alginate membrane beads containing a mechanical support in the hollow core. Macroporous Celite C-560 particles obtained from Manville, Inc. and having a diameter in the range of from about 0.4 to about 0.5 mm were suspended in 3% $CaCl_2$ solution containing the material to be encapsulated. Celite particles were removed from the $CaCl_2$ solution and excess solution was removed by soaking on a paper towel. The material to be encapsulated was entrapped in the macropores of the Celite particles. These moist particles were added to a 0.25% sodium alginate (Sigma A 7128, type IV) solution. A capsular membrane forms instantaneously due to the cross-linking of the interfacial alginate molecules by $Ca^{+2}$ cations. The membrane completely wraps the solid Celite particle in its hollow core. The newly formed membrane beads were removed from the alginate solution and were washed to remove excess alginate using 0.1 M HEPES buffer (pH 7). Finally, these membrane beads containing rigid mechanical supports were equilibrated with the desired media.

A solution containing 0.8% sodium alginate (Sigma A 7128, type IV) is prepared and kept stirred using a magnetic stirrer at room temperature. An aqueous solution is prepared in 0.1M HEPES buffer (pH 7) with 0.1M $CaCl_2$ and 2% Blue dextran (Sigma). Blue dextran is a polymer-affinity ligand derivative comprising Cibacron Blue dye and dextran. The solution is dropped through a hypodermic needle to form droplets which fall into rapidly stirred alginate solution. A capsular membrane forms almost instantaneously due to the cross-linking of the interfacial alginate molecules by $Ca^{+2}$ cations. Prior to the removal of the membrane beads the polymer solution is diluted five-fold by adding required amount of 0.1M HEPES buffer (pH 7). This step dilutes the alginate solution outside the membrane beads and reduces the possibility of membrane beads joining each other when they are in close contact, due to the gelation of the alginate solution on their exterior surface. Capsules are removed from the solution and excess solution is drained using an appropriate size mesh. The membrane beads are transferred to 0.1M HEPES buffer (pH 7) containing 0.1M $CaCl_2$ and incubated for one minute to stabilize the exterior surface. Finally membrane beads are equilibriated with the desired media. Membrane beads containing encapsulated polymeraffinity ligand derivative can be used as an affinity absorbent for separating a wide variety of proteins which interact with Cibacron Blue.

As this invention may be embodied in several forms without departing from the spirit or essential characteristics thereof, the present embodiment is therefore illustrative and not restrictive, and since the scope of the invention is defined by the appended claims, all changes that fall within the metes and bounds of the claims or that form their functional as well as conjointly cooperative equivalents are therefore intended to be embraced by those claims.

What is claimed is:

1. A method for encapsulating material within a membrane bead comprising the steps of:
   (a) suspending a first material to be encapsulated in a medium which is compatible with the material and which comprises an effective amount of gelling inducer;
   (b) forming said suspension into a droplet containing said material, said droplet having an outer surface portion;
   (c) mixing a second material to be encapsulated in a gelling solution comprising an effective amount of a gel forming polymer which polymer gels on contact with said gelling inducer, wherein said second material is a material selected from the group consisting of biological materials and suspended particles; and
   (d) forming a membrane bead including an interior portion and a gel membrane by contacting said outer surface portion of said droplet with said gelling solution for a time sufficient for said gel forming polymer to form a gel membrane at said surface portion of said droplet to a desired thickness, said interior portion containing said first material and said gel membrane being capable of encapsulating said second material therewithin.

2. The process of claim 1 wherein said first material comprises a biological material and said medium is an aqueous medium physiologically compatible therewith.

3. The process of claim 2 wherein said second material is a biological material.

4. The process of claim 3 wherein said gelling inducer comprises a polyvalent ion.

5. The process of claim 4 wherein said aqueous medium comprises a viscosity enhancer.

6. The process of claim 5 wherein said first biological material is selected from the group consisting of tissue, organelle, plant cells, animal cells, delta cells, whole islet of Langerhans, hepatocytes, bacteria, algae, fungi, viruses, proteins and pharmaceutical compounds.

7. The process of claim 6 wherein said gel forming polymer comprises a polysaccharide gum.

8. The process of claim 7 wherein said gum comprises sodium alginate.

9. The process of claim 8 wherein said gum comprises chitosan.

10. The process of claim 9 wherein said gel forming polymer comprises polylysine.

11. The process of claim 1 wherein a portion of said gel membrane is subsequently solubilized and removed from said membrane bead.

12. The process of claim 11 wherein said gel forming polymer is an ionotropic gel forming polymer.

13. A process for encapsulating material within a hybrid membrane bead comprising the steps of:
   (a) suspending a first material to be encapsulated in a medium which is compatible with the material and which comprises an effective amount of gelling inducer;
   (b) forming said suspension into a droplet containing said first material, said droplet having an outer surface portion;
   (c) mixing a second material to be encapsulated in a gelling solution comprising an effective amount of a first gel forming polymer which gels on contact with said gelling inducer at said outer surface of said droplet and a second gel forming polymer, wherein said second material is a material selected from the group consisting of biological materials and suspended particles; and
   (d) forming a membrane bead including an interior portion and a gel membrane by contacting said outer surface layer of said droplet with said gelling solution for a time sufficient for said gelling solution to gel to a desired thickness, said interior portion containing said first material and said gel membrane being sufficient to entrap said second material and said second gel forming polymer therein.

14. The process of claim 13 wherein said first material comprises a biological material and said medium is an aqueous medium physiologically compatible therewith.

15. The process of claim 13 wherein said second material comprises a biological material.

16. The process of claim 13 wherein the core of said membrane bead includes a mechanical support.

17. The process of claim 13 wherein said first gel forming polymer comprises a gel forming polymer and said gelling inducer comprises an inorganic material.

18. The process of claim 17 wherein said aqueous medium comprises a viscosity enhancer.

19. The process of claim 18 wherein said biological material is selected from the group consisting of tissue, organelle, plant cells, animal cells, delta cells, whole islet of Langerhans, hepatocytes, bacteria, algae, fungi, viruses, proteins, and pharmaceutical compounds.

20. The process of claim 17 wherein said gel forming polymer comprises a polysaccharide gum.

21. The process of claim 20 wherein said gum comprises sodium alginate.

22. The process of claim 20 wherein said gum comprises chitosan.

23. The process of claim 13 wherein said second material comprises an inorganic material.

24. The process of claim 13 wherein said second gel forming polymer comprises a thermal gel forming polymer.

25. The process of claim 24 wherein said thermal gel forming polymer comprises agarose.

26. The process of claim 13 wherein a portion of said first gel forming polymer is subsequently solubilized and removed from said membrane bead.

27. A process for encapsulating material within a hybrid membrane bead having a compartment substantially free of membrane forming polymers, said process comprising the steps of:

(a) forming a first suspension by suspending a first material to be encapsulated in a medium which comprises an effective amount of a diffusible gelling inducer for an ionotropic gel;

(b) forming a second suspension by suspending a second material to be encapsulated in a gelling solution compatible with said second material, said gelling solution comprising a selected concentration of a first, ionotropic gel forming polymer and a second gel forming polymer selected from the group consisting of a thermal gel forming polymer and a precipitation gel forming polymer, wherein said second material is a material selected from the group consisting of biological materials and suspended particles;

(c) forming said first suspension into a droplet having an outer surface portion;

(d) forming a discrete membrane bead by contacting said outer surface portion of said droplet with said second suspension for a time sufficient to form a membrane by gelling said first, ionotropic gel forming polymer and to thereby entrap said second gel forming polymer and said second material therein; and (e) gelling said second gel forming polymer entrapped in said membrane to thereby form a hybrid membrane bead.

28. The product of the process of claim 27.

29. A process for encapsulating material within a composite membrane bead comprising the steps of:

(a) suspending a first material to be encapsulated in a medium which is compatible with the material and which comprises an effective amount of gelling inducer;

(b) forming said suspension into a droplet containing said first material, said droplet having an outer surface portion;

(c) mixing a second material to be encapsulated in a gelling solution comprising an effective amount of a gel forming first polymer which gels on contact with said gelling inducer, wherein said second material is a material selected from the group consisting of biological materials and suspended particles;

(d) forming a membrane bead including an interior portion and a gel membrane by contacting said outer surface portion of said droplet with said gelling solution for a time sufficient for said gelling solution to gel at said surface of said droplet; and (e) subsequently contacting the membrane bead with a polyelectrolyte second polymer having a charge opposite to said first polymer to form a polyelectrolyte complex composite membrane therewith.

30. The process of claim 29 wherein said first material comprises a biological material and said medium is an aqueous medium physiologically compatible therewith.

31. The process of claim 30 wherein said gelling inducer comprises a polyvalent ion.

32. The process of claim 31 wherein said aqueous medium comprises a viscosity enhancer.

33. The process of claim 32 wherein said first material is selected from the group consisting of tissue, organelle, plant cells, animal cells, delta cells, whole islet of Langerhans, hepatocytes, bacteria, algae, fungi, viruses, proteins and pharmaceutical compounds.

34. The process of claim 33 wherein said first gel forming polymer comprises polysaccharide gum.

35. The process of claim 34 wherein said gum comprises sodium alginate.

36. The process of claim 36 wherein said gum comprises chitosan.

37. The process of claim 36 wherein said gel forming polymer comprises polylysine.

* * * * *